(12) United States Patent
Drasler et al.

(10) Patent No.: US 10,220,192 B2
(45) Date of Patent: Mar. 5, 2019

(54) POST DILATION BALLOON WITH MARKER BANDS FOR USE WITH STENTED VALVES

(71) Applicant: InterValve, Inc., Minnetonka, MN (US)

(72) Inventors: William J. Drasler, Minnetonka, MN (US); Mark Ungs, Minnetonka, MN (US); Wesley R. Pedersen, Minneapolis, MN (US); Scott R. Schewe, Eden Prairie, MN (US); Richard C. Kravik, Champlin, MN (US); Michael Scott Allen, Coto De Caza, CA (US)

(73) Assignee: InterValve Medical, Inc., Irvine, CA (US)

( * ) Notice: Subject to any disclaimer, the term of this patent is extended or adjusted under 35 U.S.C. 154(b) by 249 days.

(21) Appl. No.: 14/683,055

(22) Filed: Apr. 9, 2015

(65) Prior Publication Data
US 2015/0306359 A1   Oct. 29, 2015

Related U.S. Application Data

(60) Provisional application No. 61/983,377, filed on Apr. 23, 2014, provisional application No. 62/115,602, filed on Feb. 12, 2015.

(51) Int. Cl.
*A61M 25/10* (2013.01)
*A61F 2/958* (2013.01)
(Continued)

(52) U.S. Cl.
CPC ......... *A61M 25/1002* (2013.01); *A61B 90/39* (2016.02); *A61F 2/2433* (2013.01); *A61M 25/0108* (2013.01); *A61M 29/02* (2013.01); *A61B 2090/3925* (2016.02); *A61B 2090/3966* (2016.02); *A61M 2025/0004* (2013.01);
(Continued)

(58) Field of Classification Search
CPC ...... A61F 2/2427; A61F 2/243; A61F 2/2433; A61F 2/958; A61F 2002/9583; A61M 25/0108; A61M 25/10; A61M 25/1002; A61M 25/1011; A61M 25/104; A61M 2025/1004; A61M 2025/1015; A61M 2025/1059; A61M 2025/1061; A61M 2025/1068; A61M 2025/1079; A61M 2025/1086
See application file for complete search history.

(56) References Cited

U.S. PATENT DOCUMENTS 4,630,609 A * 12/1986 Chin .................. A61M 25/104
                                                                    604/101.01
4,986,830 A *  1/1991 Owens ................. A61M 29/02
                                                                    604/913

(Continued)

*Primary Examiner* — Ryan J Severson
(74) *Attorney, Agent, or Firm* — Inskeep IP Group, Inc.

(57) ABSTRACT

A bulbous valvuloplasty balloon is described that maintains its bulbous shape in its final deployed configuration along with the method of use for post dilation of a TAVR device. The bulbous balloon has two larger diameter bulb segments located on each side of a smaller diameter waist and can be used to post dilate a TAVR device that has been implanted at the site of a stenotic aortic valve. The post dilation causes deformation of the underlying tissues residing outside of the TARV stent structure.

26 Claims, 10 Drawing Sheets

(51) Int. Cl.
*A61F 2/24* (2006.01)
*A61M 25/01* (2006.01)
*A61M 29/02* (2006.01)
*A61B 90/00* (2016.01)
*A61M 25/00* (2006.01)

(52) U.S. Cl.
CPC .............. *A61M 2025/1047* (2013.01); *A61M 2025/1059* (2013.01); *A61M 2025/1079* (2013.01)

(56) References Cited

U.S. PATENT DOCUMENTS

| | | | | |
|---|---|---|---|---|
| 5,074,845 | A * | 12/1991 | Miraki | A61M 25/0119 604/101.05 |
| 5,352,199 | A * | 10/1994 | Tower | A61M 25/1002 604/103.07 |
| 5,759,174 | A * | 6/1998 | Fischell | A61F 2/91 600/433 |
| 5,868,708 | A * | 2/1999 | Hart | A61M 25/1002 604/101.05 |
| 6,270,521 | B1 * | 8/2001 | Fischell | A61F 2/95 623/1.11 |
| 6,488,653 | B1 * | 12/2002 | Lombardo | A61M 25/1002 604/101.01 |
| 6,626,861 | B1 * | 9/2003 | Hart | A61B 17/22032 604/96.01 |
| 7,618,432 | B2 * | 11/2009 | Pedersen | A61B 17/22 606/194 |
| 7,658,744 | B2 * | 2/2010 | Jackson | A61B 17/320725 606/159 |
| 7,744,620 | B2 * | 6/2010 | Pedersen | A61B 17/22 606/194 |
| 7,951,111 | B2 * | 5/2011 | Drasler | A61M 25/1002 604/100.01 |
| 8,008,395 | B2 * | 8/2011 | Zoromski | A61L 27/427 523/113 |
| 8,486,102 | B2 * | 7/2013 | Pedersen | A61B 17/22 606/194 |
| 8,685,054 | B2 * | 4/2014 | Aggerholm | A61M 25/1002 604/103.08 |
| 8,709,075 | B2 * | 4/2014 | Adams | A61B 17/22012 604/96.01 |
| 8,814,826 | B2 * | 8/2014 | Foreman | A61M 25/1002 604/101.01 |
| 8,900,264 | B2 * | 12/2014 | Drasler | A61M 25/1002 604/103.07 |
| 8,998,827 | B2 * | 4/2015 | Drasler | A61M 29/02 600/587 |
| 9,186,094 | B2 * | 11/2015 | Drasler | A61M 29/02 |
| 9,242,081 | B2 * | 1/2016 | Drasler | A61M 25/1002 |
| 9,289,224 | B2 * | 3/2016 | Adams | A61B 17/22012 |
| 9,375,555 | B2 * | 6/2016 | Pedersen | A61B 17/22 |
| 9,498,151 | B2 * | 11/2016 | Drasler | A61M 29/02 |
| 9,504,807 | B2 * | 11/2016 | Drasler | A61M 25/1002 |
| 9,511,209 | B2 * | 12/2016 | Drasler | A61M 25/104 |
| 9,592,119 | B2 * | 3/2017 | Tilson | A61F 2/2433 |
| 9,814,476 | B2 * | 11/2017 | Adams | A61B 17/22012 |
| 2005/0075662 | A1 * | 4/2005 | Pedersen | A61B 17/22 606/194 |
| 2005/0075723 | A1 * | 4/2005 | Schroeder | A61B 17/00234 623/2.1 |
| 2005/0090846 | A1 * | 4/2005 | Pedersen | A61B 17/22 606/159 |
| 2005/0137621 | A1 * | 6/2005 | Stahl | A61M 25/1002 606/194 |
| 2006/0129093 | A1 * | 6/2006 | Jackson | A61B 17/320725 604/96.01 |
| 2007/0072978 | A1 * | 3/2007 | Zoromski | A61L 27/427 524/430 |
| 2008/0249461 | A1 * | 10/2008 | Foreman | A61M 25/1002 604/28 |
| 2009/0254113 | A1 * | 10/2009 | Nolan | A61L 29/06 606/194 |
| 2010/0094209 | A1 * | 4/2010 | Drasler | A61M 25/1002 604/95.04 |
| 2010/0228277 | A1 * | 9/2010 | Pedersen | A61B 17/22 606/194 |
| 2011/0106115 | A1 * | 5/2011 | Haselby | A61B 5/076 606/151 |
| 2011/0218564 | A1 * | 9/2011 | Drasler | A61M 25/1002 606/192 |
| 2012/0083809 | A1 * | 4/2012 | Drasler | A61M 25/1002 606/159 |
| 2012/0277785 | A1 * | 11/2012 | Aggerholm | A61M 25/1002 606/194 |
| 2013/0190796 | A1 * | 7/2013 | Tilson | A61F 2/2433 606/192 |
| 2013/0261655 | A1 * | 10/2013 | Drasler | A61M 29/02 606/194 |
| 2013/0289607 | A1 * | 10/2013 | Pedersen | A61B 17/22 606/194 |
| 2015/0045826 | A1 * | 2/2015 | Drasler | A61M 25/1002 606/194 |
| 2015/0066069 | A1 * | 3/2015 | Drasler | A61M 25/1002 606/194 |
| 2015/0173898 | A1 * | 6/2015 | Drasler | A61F 2/2433 623/2.18 |
| 2015/0196230 | A1 * | 7/2015 | Drasler | A61M 29/02 600/424 |
| 2015/0306359 | A1 * | 10/2015 | Drasler | A61M 25/0108 606/191 |
| 2016/0066819 | A1 * | 3/2016 | Drasler | A61M 29/02 600/424 |
| 2016/0136399 | A1 * | 5/2016 | Drasler | A61M 25/1002 606/194 |
| 2016/0287270 | A1 * | 10/2016 | Pedersen | A61B 17/22 |

* cited by examiner

POST DILATION BALLOON WITH MARKER BANDS FOR USE WITH STENTED VALVES

RELATED APPLICATIONS

This application claims priority to U.S. Provisional Application Ser. No. 61/983,377 filed Apr. 23, 2014 entitled Echogenic Marker Bands, and U.S. Provisional Application Ser. No. 62/115,602 filed Feb. 12, 2015 entitled Post Dilation Balloon and Method Following Stented Valve Implant, both of which are hereby incorporated herein by reference in their entireties.

BACKGROUND

This application incorporates the following patents and applications herein by reference: U.S. patent application Ser. No. 12/576,970 filed Oct. 9, 2009 entitled Valvuloplasty Catheter And Methods (now U.S. Pat. No. 7,951,111 issued May 31, 2011; U.S. patent application Ser. No. 10/846,613 filed May 14, 2004 entitled Valvuloplasty Devices And Methods (now U.S. Pat. No. 7,744,620 issued Jun. 29, 2010; U.S. patent application Ser. No. 13/231,807 filed Sep. 13, 2011 entitled Positionable Valvuloplasty Catheter; U.S. patent application Ser. No. 13/766,464 filed Feb. 13, 2013 entitled Ellipticity Measuring Device; U.S. patent application Ser. No. 14/452,426 filed Aug. 5, 2014 entitled Bulbous Balloon With Mechanical Pressure Regulator; and U.S. Patent Provisional Application No. 61/983,377 filed Apr. 23, 2014 entitled Echogenic Marker Bands.

Valvuloplasty balloon catheters have been used to post-dilate stented valves that have been placed via transcatheter aortic valve replacement (TAVR) procedures. A valvuloplasty balloon is placed within the stented valve and dilated after the TAVR device has already been delivered across the site of the stenotic native aortic valve. Such post dilation has been noted to place the stent structure into more direct contact with the surrounding tissue including the native aortic valve leaflets and calcium nodules associated with the leaflets, the aortic sinus, and left ventricular outflow tract (LVOT), and thereby reduce the amount of blood leakage around the perimeter of the stented valve.

For self-expanding (SE) TAVR devices the post dilation step can ensure that underlying tissue such as the native valve leaflets and calcium nodules are fully expanded or deformed via the post dilation valvuloplasty procedure. This tissue deformation provides not only improved area for blood flow through the replaced valve but also provides a reduction in perivalvular leaks (PVL) between the stent structure and the native aortic valve tissues.

For balloon expandable (BE) TAVR devices, post dilation may be performed less often than with SE stented valves; a post dilation of a BE device can provide a larger stent diameter, more stent deformation, and provide a greater deformation of the leaflet tissues and calcium deposits underlying the stent structure. Such deformation of the BE stent can place the stent into more intimate contact with the native tissues along a perimeter of the stent resulting in a reduction in perivalvular leaks.

The native annulus can be generally interpreted as a narrowing in the aortic root located at the base of the native valve leaflets; the annulus is positioned at the base of the aortic sinus adjacent the left ventricular outflow tract (LVOT). Post dilation of a TAVR device with a cylindrical balloon is limited due to the inability to deform the native leaflets and other restrictions on either side of the native valve annulus without applying undue excessive forces upon the annulus that can lead to annular rupture or dissection. What is needed is a balloon that can post dilate a TAVR device by deforming the native valve leaflets and other restrictive tissues located outside of the TAVR stent structure while ensuring that the native annulus is not exposed to excessive forces that can cause the annulus to rupture or dissect; such a balloon would contribute to greater reduction of PVL and would provide additional safety to the patient by reducing the likelihood of annular rupture.

Stand-alone balloon aortic valvuloplasty (BAV) and transcatheter aortic valve replacement (TAVR) are performed to treat patients suffering from aortic valve stenosis. The BAV procedure can also performed prior to the TAVR procedure as a pre-dilation prior to delivery of the TAVR device or after implantation of the TAVR device as a post-dilation to reduce the amount of perivalvular leakage; BAV also provides a bridge to a TAVR procedure that can be initiated at a later date. During the implantation of the TAVR device it is important to place a TAVR device that has the correct diameter, i.e., one that provides an appropriate diametric fit with the aortic valve annulus. Additionally, it is important to locate the TAVR device along the axis of the aortic sinus such that it is in proper axial position with the basal ring or plane containing each nadir for each of the three native valve leaflets. Further, it is important to identify the angle of the axis of the aortic sinus (sinus of Valsalva) and align the TAVR device such that it is in alignment with the axis of the aortic sinus.

Typically a CT scan is performed prior to the TAVR procedure to identify the diameter of the annulus and examine the suitability of the patient for the TAVR procedure. CT measurement of the annulus diameter is not performed in real time and is not performed under a stretched condition such as found during the implantation of the TAVR device; the presence of calcium can make it difficult to accurately measure the true diameter of the annulus. The orientation of the plane of the basal ring and the axis of the annulus is difficult to identify accurately using CT scan alone.

Often transesophageal echo (TEE) or transthoracic echo (TTE) is used to visualize the aortic annulus and determine its diameter in order to properly size the TAVR device that is to be implanted. Due to the ovality of the annulus and inaccuracies in identifying the axis of the aortic sinus and the proper location of the basal plane of the annulus, an error in the diameter measurement for the aortic annulus can exceed 2-3 mm.

What is needed is a device that can accurately locate the plane of the basal ring of the annulus and identify an accurate stretch diameter of the annulus to allow accurate sizing and placement of the TAVR device in real time. Such a device can also be used to measure a diameter of any tubular member in the body in real time using 2D or 3D echo. For example, the device can be used to accurately measure the diameter of other annuli of the heart, measure diameter of a blood vessel, or the diameter of any tubular member of the body.

SUMMARY OF THE INVENTION

One embodiment of the present invention is directed to a bulbous valvuloplasty balloon that maintains its bulbous shape in its final deployed configuration along with the method of use for post dilation of a TAVR device. The bulbous balloon has two larger diameter bulb segments located on each side of a smaller diameter waist; the bulbous balloon is used to post dilate a TAVR device that has been implanted at the site of a stenotic aortic valve; the post dilation causes deformation of the underlying tissues residing outside of the TARV stent structure.

In one embodiment the bulbous balloon is formed having a single chamber that provides expansion of the waist and each of the bulbs out to form a bulbous shape at the same time when inflated to approximately 2-3 atm (range 0.5-4 atm).

In another embodiment the bulbous balloon is formed with a single chamber but the distal bulb is designed to inflate earlier than the proximal bulb. This graded inflation can be accomplished by altering the compliance of the distal bulb such that it is more compliant than the proximal bulb; such a balloon construction will allow the more compliant distal bulb to inflate first and position itself at the upstream end of the aortic annulus. Alternately, the distal bulb can be formed from a noncompliant plastic material that has a larger diameter than the waist; the distal bulb inflates first at a low pressure ranging from zero to 0.5 atm; the proximal bulb is formed from a material that is semi-compliant and requires higher pressures to cause it to inflate later to its fullest diameter.

Another embodiment of the present invention has a bulbous balloon comprised of two chambers such that the distal bulb is inflated first via one chamber and the proximal bulb is inflated secondly via a second chamber; the waist could be associated with either the first or second chamber.

In yet another embodiment of the present invention any of the bulbous balloon embodiments described in the earlier patents and patent applications made reference to herein can be used via the methods described herein to post dilate a TAVR device.

In one embodiment for a method of use the bulbous balloon of the present invention the balloon is used to post dilation of a TAVR device. In this embodiment the bulbous balloon is positioned such that the bulbous balloon waist is located adjacent the native aortic annulus. The distal bulb (for example, when the device is used via the femoral access approach) is located in the LVOT just upstream of the aortic annulus; the proximal bulb is located in the aortic sinus just downstream of the aortic annulus. This position allows a lower outward force to be applied via the balloon waist through the TAVR stent structure to the aortic valve annulus than would be applied to the annulus if a cylindrical balloon (of the same diameter as the bulbous balloon bulb) were used to post dilate the TAVR device. This lower force applied via the bulbous balloon waist upon the annulus provides a safety to the patient by reducing the likelihood for aortic annulus rupture. The proximal bulb of the bulbous balloon will apply a greater outward force (i.e., greater than a cylindrical balloon having a diameter equal to the diameter of the bulbous balloon waist) through the TAVR stent structure and onto the native valve leaflets to cause greater deformation force to push the native valve leaflets and associated calcium nodules outwards into the aortic sinus; this tissue deformation will result in an improved native valvuloplasty and improved approximation of the TAVR stent structure with the native tissues resulting in a reduction in PVL. The distal bulb of the bulbous balloon will apply a greater outward force (greater than a cylindrical balloon of the same diameter as the bulbous balloon waist) through the TAVR stent structure and onto the tissues of the LVOT just upstream of the native valve annulus causing deformation of native tissues and improving the approximation of the stent structure with the tissues of the LVOT resulting in reduction in PVL.

In another embodiment for a method of use, the bulbous balloon of the present invention (for post dilation of a TAVR device) is positioned such that the bulbous balloon waist is located adjacent the base of replacement leaflets located within and attached to the TAVR device. This position of the bulbous balloon protects the base of the replacement leaflets from excessive dilation due to the lower outward force applied by the smaller diameter waist. The proximal bulb of the bulbous balloon is located adjacent the native leaflet tips (i.e., the leaflet free edges) and can apply an outward force through the TAVR stent structure to further dilate the native valve leaflets outwards to deform them further and reduce the likelihood for PVL. The distal bulb of the bulbous balloon is located with its largest diameter aspect just upstream of the aortic annulus; this distal bulb assists in deforming the underlying tissues of the LVOT and ensures that the inflow end of the TAVR device along with the sealing surface of the TAVR device makes a good approximation with the surrounding tissues and reduces likelihood of PVL.

In another embodiment for the method of use, the distal bulb of a bulbous balloon is inflated first to position the distal bulb in the LVOT just upstream of the annulus and within the inflow region of the TAVR device. Such positioning of the distal bulb fixes the TAVR structure within the LVOT and aortic root such that it is not likely to migrate downstream due to blood flow and blood pressure generated by the LV. Further inflation of the bulbous balloon allows the proximal bulb to inflate and provide force through the TAVR stent structure to deform the native valve leaflets further and provide improved apposition of the stent structure with the outlying tissues and result in reduced PVL. The smaller diameter waist of this embodiment provides a lower outward force through the TAVR stent structure onto the annulus to protect the annulus from annular rupture.

Radiopaque markers can be placed on the outside surface of the bulbous balloon of the present invention to help ensure alignment of the balloon axis with the axis of the aortic annulus. A circular ring located at the center of the waist will assist in ensuring that the waist is positioned axially adjacent the appropriate native tissue such as the annulus or adjacent an aspect of the TAVR device such as the center of the TAVR skirt located across the native annulus.

A balloon having a bulbous shape or hour-glass shape can have advantages for positioning the smaller diameter waist of the balloon adjacent the narrow basal ring or annulus of an aortic valve. The larger bulbous portions of the balloon can assist in providing improved dilation of stenotic aortic valve leaflets as well as providing alignment of the balloon with the LVOT and aortic sinus of the heart. This alignment of the balloon axis with the axis of the annulus, aortic sinus, and LVOT can help the physician to ensure proper alignment of a subsequently placed TAVR device. The positioning of the waist along the axis of the aortic sinus and LVOT can also assist in locating the TAVR device properly such that the TAVR device is not positioned too low toward the LVOT or to high towards the aorta. The waist of the balloon will position itself adjacent to the plane of aortic valve annulus or basal ring of the aortic valve.

The bulbous balloon also has distinct advantages for post-dilation of a TAVR device in comparison to a standard cylindrical device. The larger diameter bulbous portions of the balloon exerts an outward force and displacement against the frame of the TAVR device and also against the underlying native leaflets and LVOT tissues to undergo a larger deformation of the tissues than what would be experienced from a standard cylindrical balloon. The smaller diameter waist of the bulbous balloon exerts a smaller outward force against the frame of the TAVR device that is adjacent to the valve annulus and thereby protects the annulus from excess expansion and rupture in comparison to the larger forces exerted against the annulus by a cylindrical balloon.

To assist in the accurately determining the axial position and alignment of the balloon within the LVOT, annulus, and aortic sinus, markers can be place around the circumference of the bulbs and/or the waist of the balloon. These markers can be radiopaque (RO) markers that are able to absorb x-ray energy and can be visualized with fluoroscopy or they can be echogenic markers that that can be seen via 2D or 3D echo. The markers can be adhered or bonded to the balloon as a solid band that encircles the balloon or the markers can be a discontinuous band comprised of a series of dots or dashes that extend around the circumference of the balloon.

When the balloon and marker bands are viewed under fluoroscopy (fluoro) or echo cardiography (echo) in a direction perpendicular to the axis of the balloon, the circumferentially placed marker band will appear as a line. When viewed under fluoro or echo, the marker band will help the observer to view a plane that is actually perpendicular to the axis of the aortic sinus. When viewed from an oblique angle under fluoro with respect to the axis of the balloon, the circumferential marker band will appear oval. Viewing under fluoroscopy or echo, the marker band located around the circumference of the bulb located in the LVOT allows the observer to measure the relative dimensions of the major and minor axis of the observed oval knowing that the bulb in the LVOT is actually a circle since it is unencumbered or not restrictive from attaining a round circumferential shape. This information can then be used to determine the actual ovality of the annulus; this is more fully described in the patent application Ser. No. 13/766,454 for RO markers; the use of a circumferential marker band to identify alignment and ovality is applicable to an echogenic band as well as for an RO band. When viewed under 3D echo from a direction perpendicular to the axis of the balloon the viewer is able to view the entire echogenic marker band and measure the diameter knowing that the diameter is in a plane that is perpendicular to the axis of the aortic root.

In an alternate embodiment, an RO marker band or echogenic band can also be placed around the circumference of a standard cylindrical balloon. Such a balloon does not provide automatic positioning of the balloon to a specific location along the axis of the aortic sinus, annulus, and LVOT. The cylindrical balloon having a marker band located around its circumference would however allow the operator to obtain improved alignment of the balloon axis with the axis of the aortic sinus, annulus, and LVOT in comparison to current techniques which rely primarily upon fluoroscopic and echo images without the benefit of such markers; the marker band can also assist in diameter measurement of the annulus due to the ability to visualize the circular shape of the marker bands easier via fluoro or echo than visualizing a 2D image of a balloon under either fluoro or echo.

An RO or echogenic marker band can be formed by direct application of a suspension of RO particles suspended in a polymeric solution to be deposited directly upon the outer surface of the balloon.

Alternately, small rubber bands formed from a composite of RO material or echogenic material, plus a polymeric material can be formed in advance and bonded to the outer surface of the balloon as a second step; bonding methods include solvent bonding, adhesive bonding, use of primers, or a variety of plasma treatment methods. Some plasma treatment methods include, for example, plasma etching and plasma deposition with a variety of gases including oxygen, ammonia, to generate active groups on the balloon outer surface that can more readily attach to the polymer material found in the band. Such rubber bands of RO material formed from particles embedded in an elastic or compliant polymer can provide stretch characteristics if desired in order to provide the waist of the bulbous balloon with an ability to grow under pressure.

An echogenic marker band can be formed from several methods. For example, air that is trapped in a polymeric material such as a foam polymer or a microporous polymer can be visualized under echo. Materials with high acoustic impedance are known to reflect sound waves. The presence of surfaces having a large dimension in comparison to the wavelength of the sound waves being used (typically 0.1-0.5 mm for frequencies of 15-3 MHz), and having an acoustic impedance that differs from the surrounding tissues will reflect the echo signal well and will be seen on echo. Smaller particle diameter relative to the wavelength will cause the echo signal to be scattered and attenuated. Particles that can be used as echogenic materials include spherical polymeric particles, glass particles, and gas-filled particles, metal particles, flattened particles, foam particle, and others. A resonating material that has a natural resonant frequency similar to that being used to form the echo image (i.e., 3-15 MHz) will also absorb energy of the echo and will be easily seen by echo; such resonating particles can also be added to polymeric solution to form a suspension that can be deposited around the circumference of a balloon to form a strip or echogenic band. Such resonating material includes polymer molecules, polymer particles, organometallic molecules or particles, metallic molecules or particles that have a resonant frequency of approximately 2-20 MHz or a multiple thereof. Echogenic particles can also be formed into a polymer suspension that forms a ring that can be placed on the outside of a balloon circumference and bonded to the balloon as a second step.

A band also can be formed from an electrically conductive material. The electrically conductive material can be formed from a concentrated suspension of metallic particles within a polymeric holding medium. The particles can be tungsten, silver, platinum, tantalum or other conductive metal that can be spherical, pebble-shaped or shaped like a flat flake and in contact with a neighboring particle or in contact with a conductive polymeric medium such as an ionic polymer, for example, to transmit electrical current through the suspension. The electrically conductive material can also be wire that is configured to stretch and conform to the diametric expansion of the balloon. A wire, for example, can be configured into a zig-zag shape or a small spiral shape and then bonded to the surface of the balloon. Following the application of the electrically conductive band to the outside of the balloon, an electrical current can be directed via a delivery wire that extends through the shaft of the catheter to generate an oscillatory current or alternating current signal with a frequency that is interactive with the ultrasound signal used for the echogenic imaging of the heart, typically ranging from 2-20 MHz.

Echogenic particles or RO particles can also be formed into a polymer suspension that forms a ring that can be placed on the outside of a balloon circumference and bonded to the balloon as a second step. The RO ring or an echogenic ring can be formed from a flat membrane of suspension material or from a cylinder of suspension material that has been cured to allow removal of any solvent present during the processing of the flat or cylindrical membrane. The polymeric membrane containing the RO or echogenic particles can then be cut into strips and then bonded to the outer surface of the balloon using methods described earlier. If echogenic particles are placed into the band, the particles can be chosen to either absorb the echogenic signal, to generate an echogenic signal via a natural frequency similar to the frequency of the echo, to reflect the echogenic signal, or to transmit a current with a frequency similar to the echogenic signal used to view the tissue of the body.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
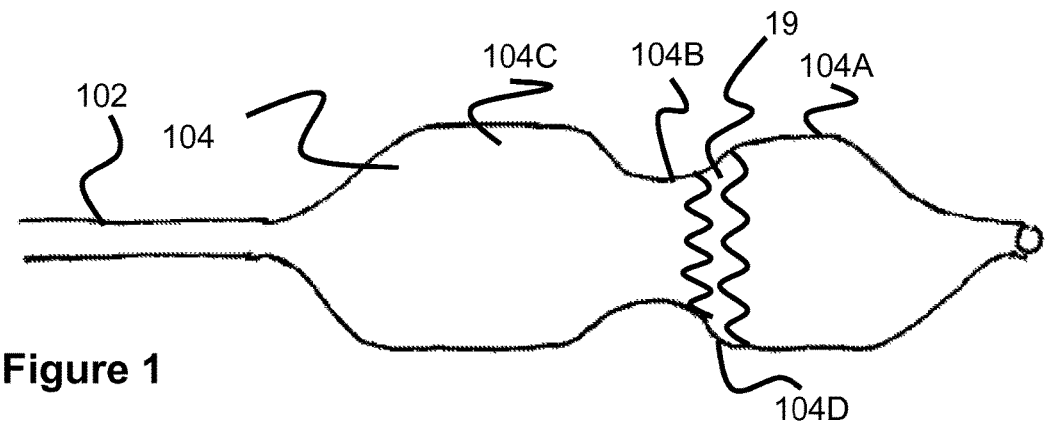
FIGS. 1 and 2A-2B illustrate various aspects of a bulbous balloon.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Post Dilatation Balloon and Procedure

A bulbous balloon of the present invention includes a bulbous shape that is maintained (i.e., does not transform into a cylindrical shape upon inflation to it normal working pressures) when it is inflated to its final deployment state at a pressure of, for example, approximately 2-3 atm (range 1-4 atm). The bulbous balloon can have a variety of constructions as described in any of the referenced patents and patent applications.

One embodiment of the bulbous balloon 104 of the present invention is shown in FIG. 1. The materials of construction for the balloon 104 can be nylon, Pebax, PET, polyurethane, braided or unbraided, and other constructions as described in the referenced patents and patent applications. Upon inflation to a working pressure of 1-4 atm the distal bulb 104A and proximal bulb 104C have a diameter that ranges from 20-30 mm and the waist of the bulbous balloon ranges from 16-25 mm; the waist 104B diameter for each balloon 104 being smaller than the bulb diameter by 2-7 mm. In this embodiment, the bulbous balloon 104 has a single chamber and the entire balloon has a uniform pressure found throughout its interior.

Figure 2A:
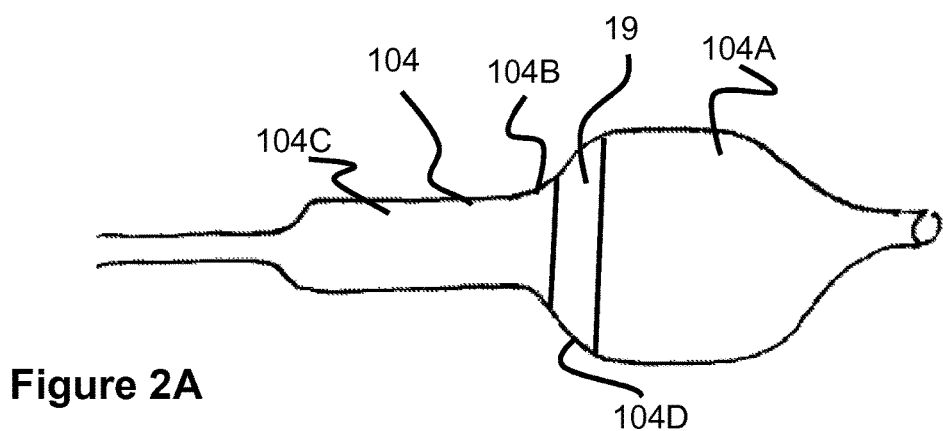
Figure 2B:
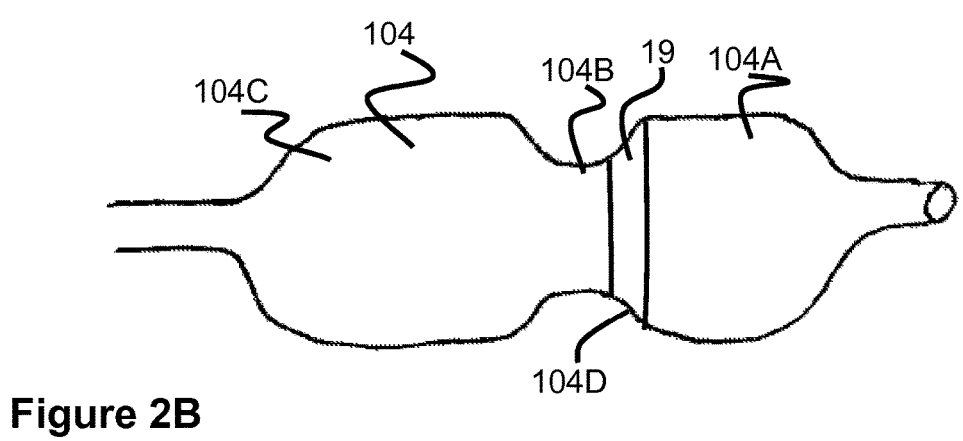

In another embodiment as shown in FIGS. 2A and 2B and also described in the referenced patents and applications, the balloon has a single chamber, but the distal bulb 104A is constructed such that it inflates at a lower pressure than the proximal bulb 104C. The distal bulb 104A, for example, can be formed from a more compliant material than the proximal bulb 104C such that a lower pressure (range 0.2-1.0 atm) will cause the distal bulb 104C to inflate to fully inflated diameter (range 20-30 mm) before the proximal bulb 104C as shown in FIG. 2A. Upon inflation to a higher pressure (range 0.5-4 atm) the proximal bulb 104C inflates to a fully inflated diameter as shown in FIG. 2B. The waist 104B is maintained at a smaller diameter than either of the bulbs in its fully inflated configuration. A variety of construction materials and wall dimensions can be used to provide this difference in compliance.

Alternately, the construction of the balloon shown in FIGS. 2A and 2B can be such that the distal bulb 104A is formed from a noncompliant material having a natural large diameter configuration that is formed at low pressure (range zero to 0.2 atm). The proximal bulb 104C can be formed with a semi-compliant material that provides a smaller diameter such as shown in FIG. 2A at low pressures (range zero to 0.5 atm) and enlarges to a fully inflated diameter (range 20-30 mm) at pressures ranging from 0.5-4 atm as shown in FIG. 2B.

The balloon of FIG. 2A can also be constructed such that it maintains the shape as shown in this figure, having a larger diameter distal bulb 104A and a smaller diameter cylindrically shaped proximal bulb 104C. The distal bulb 104A has a diameter that is larger than the aortic annulus by approximately 5 mm (range 3-7 mm) and ranges in diameter from 22 to 30 mm. The proximal bulb 104C has a diameter that is slightly smaller than the annulus and ranges from 17 mm to 27 mm. Upon inflation of the balloon to 0.5 to 1 atm the distal bulb 104A can be positioned adjacent and upstream of the aortic annulus in the LVOT and can push any tissue or materials of a stent valve frame outwards into contact with the LVOT. Further inflation of the balloon can cause the proximal bulb 104C to make contact with the annulus, tissue, or materials of a stent valve frame that is located adjacent the annulus. A semi compliant material such as Nylon or Pebax can be used to construct this balloon, for example.

As an additional embodiment, a balloon expandable (BE) stent 19 can be placed onto the distal waist shoulder 104D of the balloon as shown in FIGS. 1, 2A and 2B. Alternately, the BE stent 19 can be placed on the waist 104B or distal bulb 104A of the balloons of any of the embodiments of the present invention and as shown in FIGS. 3A, 3B, 4A, 4B, 5A, and 5B. Upon expansion of the balloon 104, the BE stent extends outwards to hold the materials of a stent valve frame outwards against the stent valve frame to force it into intimate contact with the surrounding tissues and thereby close any perivalvular leak (PVL) that my exist between the stent valve frame and the tissues of the annulus or LVOT. The BE stent can be of any construction currently used in the medical device industry. The structure often involves a zig-zag pattern that opens up upon expansion. The material of the stent can be stainless steel, cobalt cromium, or other plastically deformable metal. The axial length of the stent can be short, ranging from 3 mm to 10 mm to minimize the contact of the stent with the leaflets of a stent valve or excessive contact with the tissues of within the LVOT.

Figure 3A:
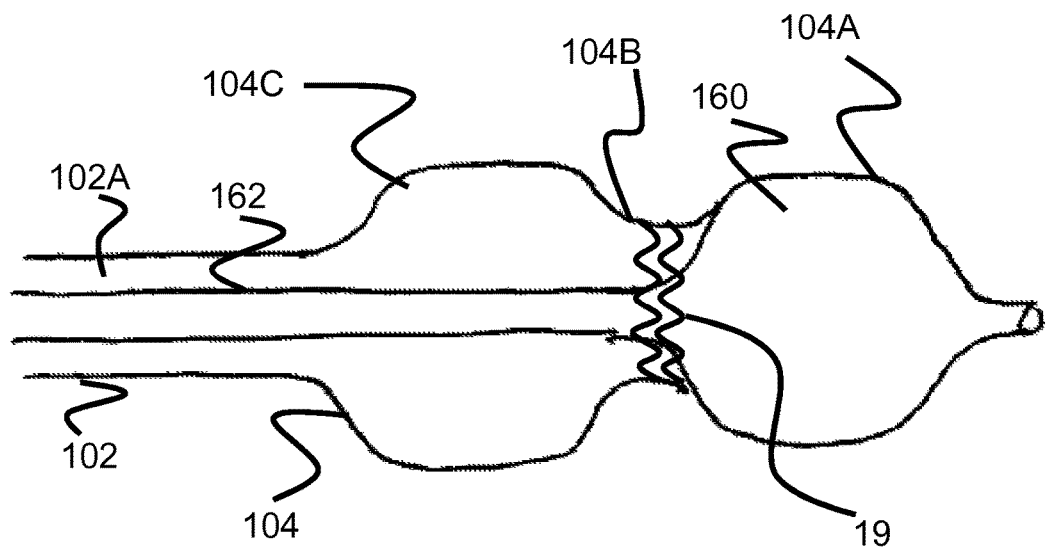
FIGS. 3A-3B illustrate various aspects of a bulbous balloon with an inner, secondary balloon.
Figure 3B:
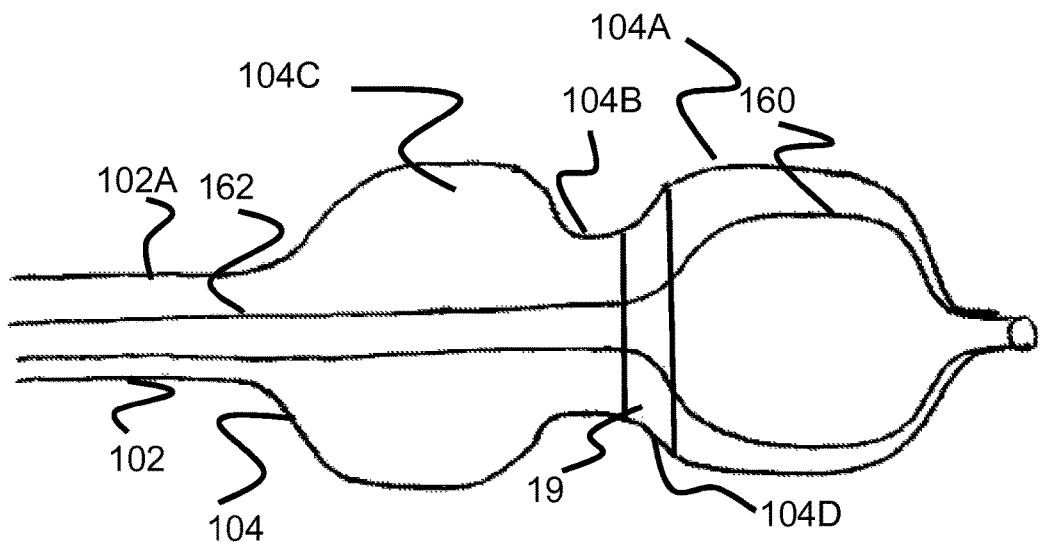

Further embodiments for the bulbous balloon are shown in FIGS. 3A and 3B; such embodiments have two chambers within the balloon. The construction of such balloon embodiments are described in more detail in the referenced patents and applications. The presence of two chambers allows the distal bulb 160 to be inflated first to allow positioning of the distal bulb at a location just upstream of the native annulus. The proximal bulb 104c can be inflated second to dilate the native leaflets of the aortic valve and to push a TAVR frame into intimate contact with the surrounding tissues to reduce PVL. The presence of two chambers also allows one chamber to be inflated at a different pressure than the other, if desired.

In FIG. 3A, an inner distal bulb 160 has a distal inflation lumen 162 that allows inflation of the distal bulb 104A to its fully inflated diameter (range 20-30 mm) while the proximal bulb 104C is still uninflated (not shown as uninflated). The distal bulb 104A can be formed, for example, from a semi-compliant material or a noncompliant material. As a second step, the proximal bulb 104C can be inflated (0.5-4 atm) via a proximal inflation lumen 102A within the catheter 102 to cause the proximal bulb 104C to attain its fully inflated diameter as shown in FIG. 3A.

FIG. 3B shows another embodiment of a two chamber bulbous balloon having a first inner distal bulb 160 that is inflated before the outer proximal bulb 104C via a distal inflation lumen 162. The inner distal balloon 160 can be formed from a semi-compliant or noncompliant material, for example. The inner distal bulb 160 is inflated via the distal inflation lumen 162 to 0.2-1 atm to position the inner distal bulb 160 at a location just upstream of the native valve annulus. As a second step, the outer balloon 104 having a bulbous shape is inflated via the bulbous inflation lumen 102A to form an outer bulbous balloon. The outer bulbous balloon has a larger diameter (range 20-30 mm) distal and proximal bulb that is maintained larger than the diameter of the waist (range 16-25 mm). The outer bulbous balloon is constructed of semi-compliant or noncompliant polymeric material. A stent 19 located on the waist of the balloon (see FIG. 3A) or on the distal waist shoulder 104D (see FIG. 3B) is expanded into contact with the frame of a TAVR device to hold the frame outwards into contact with the surrounding tissues to reduce PVL.

FIGS. 4A-5B show methods of use for the bulbous balloon embodiments described in the present patent application and described in the referenced patents and applications. A native valve annulus 11 is presently defined as a planar ring located at the junction of the nadirs (or lowest native leaflet 14 attachments located nearest the left ventricle outflow tract 20) of the three native valve leaflets 14 with the tubular vessel wall located between the base of the aortic sinus 12 and the LVOT 20. A TAVR device 18 is shown extending from the LVOT 20 across the annulus 11 and through at least a portion of the aortic sinus 12. The inflow end of the TAVR device extends upstream from the annulus 11 for a few mm (range 1-7 mm) into the LVOT 20. For self-expandable TAVR devices, the TAVR stent frame 18 often extends downstream from the annulus 11 through the aortic sinus 12 and into a portion of the aorta. For balloon expandable TAVR devices, the TAVR stent 18 often extends downstream from the annulus 11 across at least a portion of the aortic sinus 12 and across the native aortic valve leaflets 14. The native leaflets 14 are held outwards by the stent structure of the TAVR device 18. The TAVR stent structure 18 is attached to three replacement leaflets 16. The bases of the three replacement leaflets 16 forms a leaflet base; a skirt 15 is attached to the TAVR stent 18 extending from the leaflet base to the inflow end of the TAVR stent structure 18. The skirt 15 is intended to be held tightly against the vessel wall to provide a seal that prevents blood leakage from occurring in a retrograde direction across the TAVR device 18.

Figure 4A:
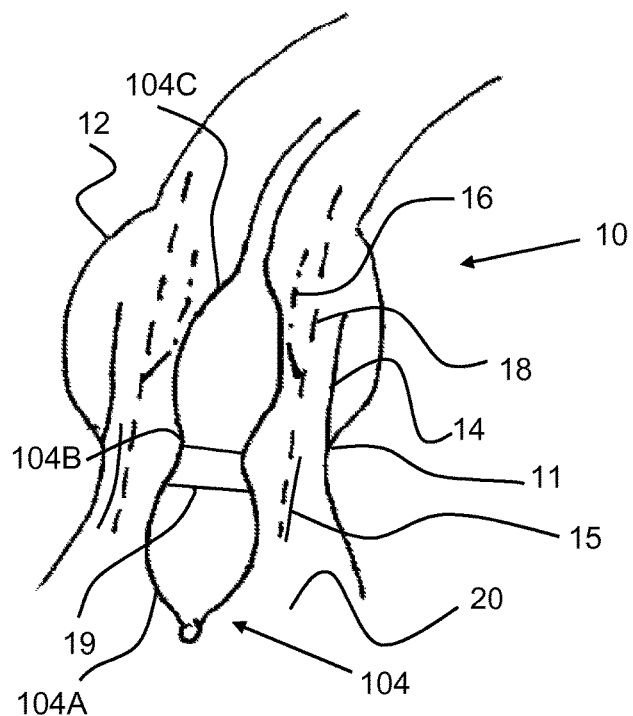
FIGS. 4A-4B and 5A-5B illustrate various aspects of a method for expanding a balloon against a TAVR device.

In FIG. 4A, the bulbous balloon 104 of the present invention is placed within a previously implanted TAVR device. In this embodiment the waist 104B of the bulbous balloon 104 is positioned adjacent to and approximately in the same plane as the aortic valve annulus 11. The distal bulb 104A of the bulbous balloon 104 is positioned upstream of the annulus 11 in the LVOT 20; the proximal bulb 104C is positioned within the aortic valve sinus 12. Expansion of the bulbous balloon 104 causes the proximal bulb 104C to generate an outward force through the TAVR device stent structure 18 and further deform or form a further valvuloplasty on the underlying native aortic valve leaflets 14 and other calcified tissues associated with the leaflets 14 or wall of the aortic sinus 12.

This further deformation of the native valve leaflets 14 and surrounding tissues allows a self-expandable or balloon-expandable TAVR stent frame 18 to better approximate the surrounding tissues to form a better seal between the skirt 15 and the surrounding tissues thereby reducing blood pathways that could lead to perivalvular leaks (PVL). For balloon-expandable TAVR devices, the stent structure or frame 18 can also be further deformed by the post dilation procedure thereby improving stent approximation with the surrounding tissues and reducing the amount of PVL. Expansion of the distal bulb 104A further expands the skirt region 15 of the TAVR stent 18 outwards generating an outwards force to further deform tissues of the LVOT 20 just upstream of the annulus 11 and neighboring the annulus thereby providing improved apposition of the TAVR stent 18 with the underlying tissues near the inflow end of the TAVR device 18 and reduce the tendency for PVL. The waist 104B of the bulbous balloon 104 has a smaller diameter than the diameter of the native annulus 11 and hence applies a lower (lower than a cylindrical balloon having equal diameter to the bulb diameter) outward force through the TAVR stent onto the annulus 11 thereby protecting the native annulus against annular rupture.

Figure 4B:
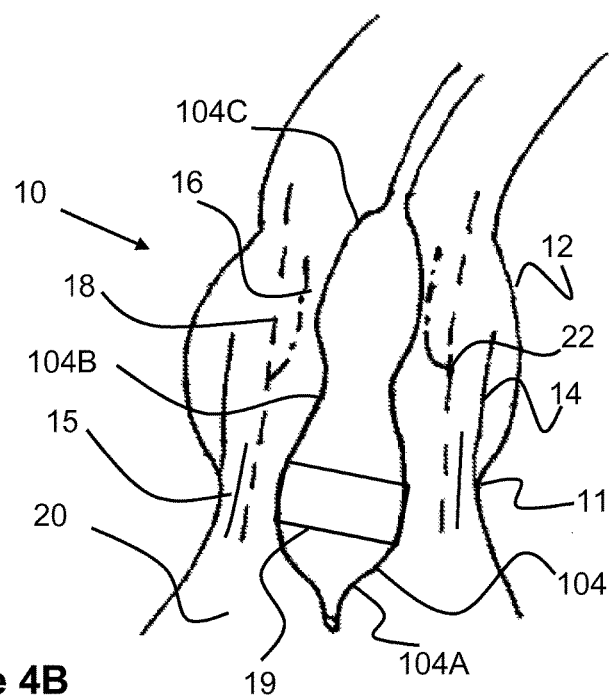

A stent 19 located on the distal waist shoulder 104D as shown in FIG. 4A can be expanded during inflation of the balloon 104 to make contact with the TAVR frame in skirt region 15 and cause the TAVR frame to make improved contact with the annulus 11 or surrounding LVOT 20 tissues and thereby close a blood leak path that can lead to PVL. Alternately, as shown in FIG. 4B a stent can be located on the distal bulb 104A. Upon expansion of the balloon 104, the stent 19 can generate an outward force against the TAVR stent structure or frame 18 to cause it to move outwards and make improved intimate contact with the tissues of the annulus or LVOT 20 along a perimeter and reduce the blood flow pathways that cause PVL.

Sizing the bulbous balloon 104, as shown in FIG. 4A, for post dilation of a TAVR device 18 such that it has a distal or proximal bulb diameter that is equal to the diameter of a cylindrical valvuloplasty balloon provides the benefit of further deforming the aortic valve leaflets 14, calcium nodules, and other surrounding tissues either upstream or downstream of the annulus 11 while protecting the annulus from rupture due to a lower outward force against the annulus than would be found by post dilating with a cylindrical balloon. Sizing the bulbous balloon as shown in FIG. 4A, for post dilation such that the bulbs are of a larger diameter than the diameter of a cylindrical balloon and the waist 104B is smaller than the diameter of a cylindrical balloon and smaller than the annulus provides a double benefit; one obtains improved deformation of the tissues adjacent the bulbs to realize an greater reduction in PVL over a cylindrical balloon and improved protection of the annulus against annular rupture compared to a cylindrical balloon.

For SE stented TAVR devices it has been found that the outward force exerted against the annulus by a NiTi stent structure sized in accordance with the instructions for use is approximately 0.5 atm (range 0.3-1 atm). Placement of a bulbous balloon 104 inside of a TAVR device 18 that was placed within an annulus 11 as shown in FIG. 4A wherein the proximal bulb diameter or distal bulb diameter was sized for use in the TAVR device 18 has demonstrated that a lower outward force is generated against the annulus than a cylindrical balloon having the same diameter as the bulb diameter.

In an alternate method of use for post dilation of a TAVR device 18 with a bulbous balloon, the placement of the balloon waist 104B can be located adjacent the leaflet base 22 for the replacement leaflets of the TAVR device as shown in FIG. 4B. Expansion of the bulbous balloon 104 allows the leaflet base of the TAVR device to be protected against possible undue expansion that could cause trauma to the replacement leaflets 16. Expansion of the distal bulb 104A to a modest inflation pressure of 1-2 atm (range 0.5-4 atm) will apply an outward force to the skirt 15 of the TAVR device 18 and place it into approximation with the surrounding tissues to form a seal that can reduce PVL. The proximal bulb 104C located in the aortic sinus will deform the native leaflet tissues and provide improved approximation of the TAVR stent with the wall of the aortic sinus and reduce PVL.

Figure 5A:
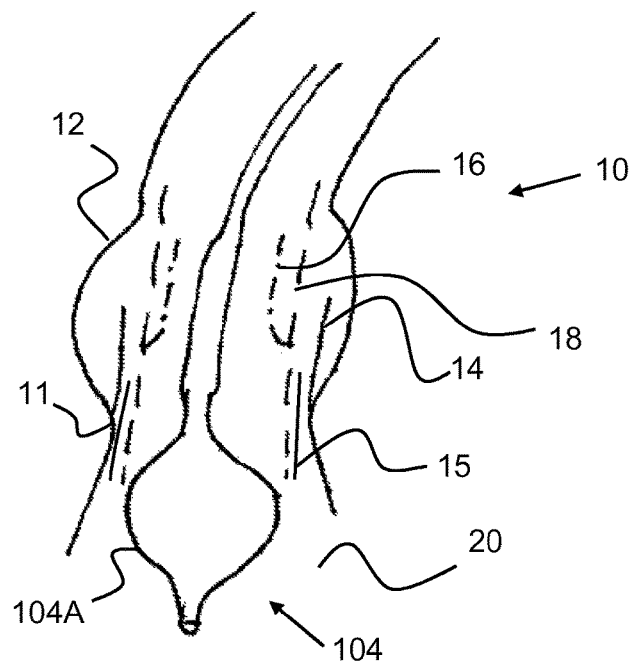
Figure 5B:
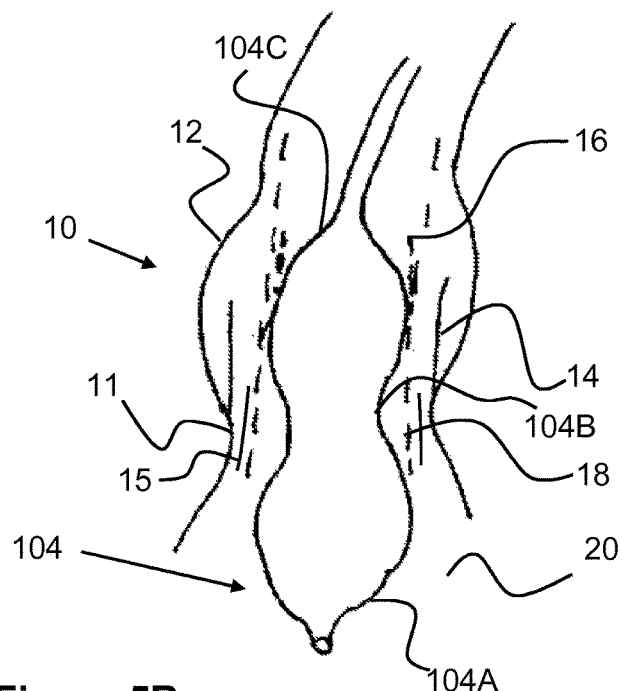

As shown in FIGS. 5A and 5B a bulbous balloon 104 that allows the distal bulb 104A to inflate prior to the proximal bulb 104C provides additional benefits when used for post dilation of a TAVR device 118. Inflation of the distal bulb 104A before the proximal bulb 104C allows the bulbous balloon 104 to position itself such that the distal bulb is located just upstream of the aortic annulus 11. During initial inflation of the distal bulb 104A within the skirted region of the TAVR device 18, the distal bulb 104A expands outwards against the skirted region 15 of the TAVR stent 18 and locks the TAVR stent structure 18 against the wall of the LVOT 20. This locking will prevent the TAVR stent 18 from migrating downstream due to blood pressure and blood flow as the remaining proximal bulb is being inflated thereafter. The position of the bulbous balloon waist 104B of this embodiment can be similar to that which was described in the embodiments of either FIG. 4A or FIG. 4B without deviating from the benefits obtained by having a bulbous balloon as described in these embodiments.

A stent located on the distal waist shoulder as shown in FIG. 4A can be expanded during inflation of the balloon to make contact with the TAVR frame in the skirt region and cause the TAVR frame to make improved contact with the annulus or surrounding LVOT tissues and thereby close a blood leak path that can lead to PVL. Alternately, as shown in FIG. 4B a stent 104D can be located on the distal bulb. Upon expansion of the balloon, the stent 19 can generate an outward force against the TAVR stent structure or frame to cause it to move outwards and hold it into intimate contact with the tissues of the annulus or LVOT along a perimeter and reduce the blood leak paths that cause PVL.

Figure 5C:
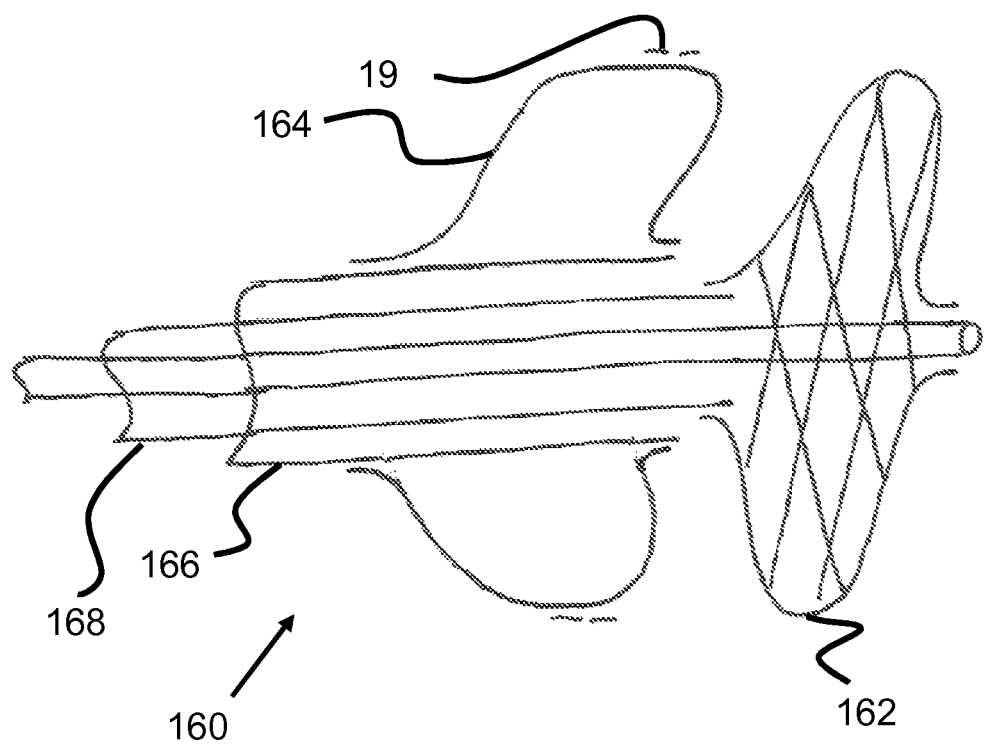
FIG. 5C illustrates various aspects of an expandable balloon with a distal expandable mesh portion.

It is understood that the distal bulb 104A of the balloon shown in FIG. 5A could alternately be a braided bulb 162 of the balloon catheter 160 that forms a bulb shape upon generating a length reduction within a braided tubular structure as shown in FIG. 5C. Such a braided distal bulb 162 located at the end of a distal bulb shaft 168 would allow blood flow to pass through it while it was being positioned adjacent and upstream to the aortic annulus. A second balloon shaft 166 having a separate expansion balloon 164 located at its distal end then passes over the distal bulb shaft 169 and is positioned in a slidable manner adjacent and downstream from the braided bulb (i.e., for femoral access and retrograde advancement through the aorta). The expansion balloon 164 then serves as the proximal bulb of the present invention to push outwards against the TAVR stent structure. A stent 19 can be located on this proximal bulb as described for the embodiments of the present invention to further supply an outward force to hold the TAVR frame outwards against surrounding tissue to prevent PVL.

Echogenic Marker Bands

Figure 6A:
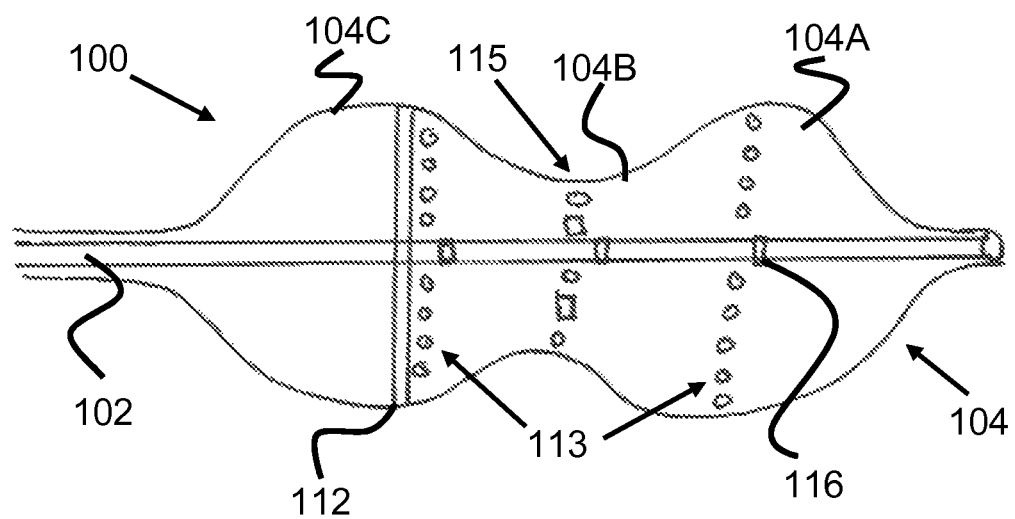
FIGS. 6A-6C and 7A-7B illustrate various aspects of different balloon embodiments having markers.

FIG. 6A shows a bulbous balloon embodiment 100 of the present invention having both radiopaque (RO) marker bands 113 and echogenic marker bands 112. Alternately the balloon 104 can have either RO markers 113 or echogenic markers 112. The bulbous balloon 104 can be formed from non-compliant materials, semi-compliant materials, compliant materials or a combination of materials as described in prior embodiments of the present application and also in other patent that are incorporated within this patent application. Such balloon materials include but are not limited to Pebax, Nylon, Polyurethane, PET, blends of polymers, and composites of polymers and fibers or structural materials that are found in balloons used in the medical device industry. The marker bands 112 and 113 can consist of a solid marker band which is placed continuously around the perimeter of the balloon or a discontinuous marker band that is comprised of dots or dashes of RO or echogenic marker material.

In one embodiment, a discontinuous marker band 115 is located in the waist region 104B of the balloon 104 and is comprised of a combination of both echogenic dots followed in series by RO dashes. Alternately, a solid band of RO or echogenic material can be located around the circumference of the waist 104B. Another set of marker bands is located on the proximal bulb 104C. There is located a solid or continuous marker band of echogenic marker material and a series of dots of RO markers located as a separate band adjacent the solid echogenic marker band. The distal bulb 104A is shown to contain a single band of echogenic dots located around its perimeter. It is understood that the bulbous balloon 104 of this embodiment can have either echogenic marker bands, RO marker bands, or both echogenic and RO marker bands located adjacent each other or formed discontinuously with each other or in any combination of solid (i.e., continuous) or discontinuous marker bands that is desired and located in the waist or one or more bulbs of the balloon.

It is noted that the bulbous balloon can also contain inner shaft RO or echogenic markers 116 located along the inner shaft of the balloon as shown in FIG. 6A. The markers can be located, for example, at the center of the waist, and located in each bulb region. The inner shaft RO markers can be located, for example in the plane of the RO or echogenic marker bands that are located on the outside surface of the balloon. In one embodiment, the inner shaft markers 116 or the marker bands 112 and 113 located on the outside of the balloon are located such that they align with a specific feature of a TAVR device (that is visualized under fluoro or echo) thereby allowing the balloon to be easily positioned within a TAVR device prior to inflation of the bulbous balloon. One position for the bulbous balloon, for example, would be to locate a marker band or inner shaft marker to align with the end of a TAVR frame; in so doing, for example, the waist of the bulbous balloon becomes centered within the sealing surface of the TAVR device, commonly referred to as the skirt of the TAVR device and also aligned with the native valve annulus.

The RO marker bands or echogenic marker bands can be formed from a composite of materials that contain RO material such as tungsten, gold, platinum, silver, platinum, iridium, tantalum, and others known in the art formed into particles and dispersed into a polymeric suspension (generally containing a polymeric solvent that is later removed via evaporation) that is formed into a thin film. Alternately a chemical reaction can be performed to cause the polymer to entrap particles or gas bubbles within the polymer to form a thin RO or echogenic layer of polymer and particles. The thin film 132 can be applied directly to the balloon 104 via syringe 130 as the balloon is rotated around its axis, as shown in FIG. 8D. Alternately, thin strips 156 (approx. 0.001-0.003 inches thick and approximately 1 mm wide (range 0.5 mm-4 mm)) can be formed on a flat surface 150 (see FIG. 9A) or cylindrical surface (see FIG. 8A) and allowed to cure generally via solvent evaporation and polymer molecular bonding. The thin strips or bands can be placed around the circumference of the balloon and bonded to the balloon; a polymeric overcoat can be applied over the balloon and band to ensure that the RO band is adequately adhered to the balloon. Such overcoat material can include Parylene, tetrafluoromethane, silica, or other thin film that is both adherent to the balloon, the marker band, and does not form a tacky outer surface to the outside of the balloon.

Echogenic marker bands can be formed from a composite of materials that contain echogenic material such as particles of porous ceramic, porous beads, polymeric spheres, hollow polymeric spheres, metal particles, metal flattened particles, gas bubbles, reflective materials, and other materials having a large difference in acoustic impedance from the surrounding tissues; these materials can be dispersed into a polymeric suspension and applied to the balloon in a manner similar to that described for the RO marker materials. The size of the particle should be approximately equal to or larger than the wavelength of the ultrasound signal that is being used to visualize the tissue of the body. Often the frequency of the sound wave is approximately 10 MHz with a wavelength of 0.15 mm (range 0.05 to 1.5 mm). The polymeric material can be formed into a suspension that contains either particles or bubbles of echogenic material. Solvent can be evaporated or extracted from the polymer and particle suspension to allow the particles or bubbles to be entrapped within the polymeric film. A chemical reaction can also be applied to entrap particles or bubbles within a polymeric film.

Alternately the echogenic marker bands can be formed from a foamed polymer or a polymer that contains entrapped gas such as air that is released as the polymeric solution or suspension or emulsion is exposed to a lower pressure or a changing temperature. Fibrous or polymeric material with entrapped gas will also serve as a good echogenic material and such materials can be entrapped within the polymeric film. Embedding spheres of hollow silica, polymeric spheres, porous spheres, ceramic spheres, carbon spheres, or other spheres having a large acoustic impedance difference from tissue within a polymeric suspension can be used to form an echogenic film or band that can be applied to the circumference of a balloon.

Applying the echogenic film or band either directly to the balloon or forming it into a band that is then applied and bonded to the outside circumference of a balloon in a second step is also a method for forming the echogenic bands onto the balloons. When the marker band is applied directly to the balloon, it is formed into a suspension that is comprised of a polymer, the echogenic particles, and a solvent. The solvent is one that is able be dissolve the polymer to form a viscous solution with high polymer solids content that will suspend the particles. Such solvents included dimethylacetamide (DMAC), tetrahydrofuran (THF), Toluene, Butanol, Isopropyl alcohol, methylene chloroide, and others. The choice of solvent can also be determined by providing a solvent capable of some dissolution of the surface of the balloon to which the band is being applied. Alternately, one may choose a solvent that cannot attack the surface of the balloon so that the balloon is not weakened; in this instance, one may choose to prepare the balloon via application of a primer, plasma etch, plasma deposition, or other application of a polymer to the outside of the balloon prior to application of the band to enhance bonding of the band to the balloon. The polymer that is found in the band can include polyurethane, Pebax, Nylon, polyethyletherphthalate (PET), and other polymers commonly used for balloons in the medical device industry. The particles are mixed into the polymer solution at a concentration ranging from 75-95% of the total weight of the solids found in the band (i.e., not including the solvent). The suspension can be applied directly onto the surface of the balloon to form a band that is either echogenic or radiopaque. Application of the suspension can be accomplished using a variety of pumps including a positive displacement pump such as a syringe pump 130, a rotary pump, a screw-type pump, or other pump that drives the suspension through a delivery tube onto the surface of the balloon 104 as shown in FIG. 8D.

When the marker band is first formed into a band and then is applied to the balloon as a second step, the marker band can be formed from a suspension that is comprised of a polymer, a solvent, and an amount of particles as described earlier for direct coating. The suspension can be formed into a flat sheet or into a tubular form and the solvent allowed to evaporate. The remaining polymer and particle film can then be cut into strips that will then be applied to the balloon as a second step. Bonding of the strips of the band material can be bonded to the balloon using a solvent, a solvent and polymer solution, an adhesive, thermal bonding, or a combination of bonding techniques. Plasma etching or plasma deposition onto the balloon can be performed to aid in the bonding.

The echogenic film can be formed from a material that has a natural resonating frequency that is similar to the frequency that is typically used for imaging the heart via TEE or TTE, i.e., 3-10 MHz (range from 2-20 MHz). Such material include but are not limited to those found in echo generating probes; some of these materials include quartz, zirconium, ceramic, and other materials including piezoelectric materials including polyvaniladine fluoride. Such resonating materials can be formed into small particles ranging from approx. 5 microns to 0.002 inches in diameter (range 1 micron to 0.004 inch). Resonating materials can be chosen to absorb or reflect sound waves with a frequency that is used for the imaging of the aortic annulus via 2D or 3D echo.

Figure 8A:
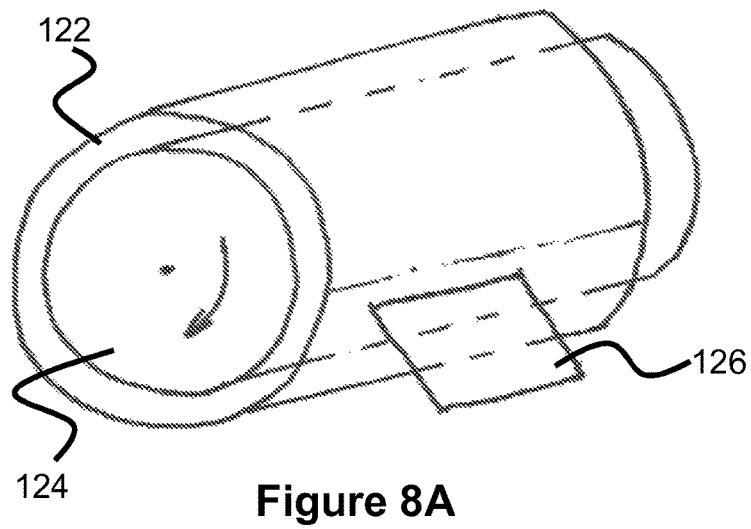
FIGS. 8A-8E and 9A-9C illustrate various aspects of creating balloons with markers.
Figure 8B:
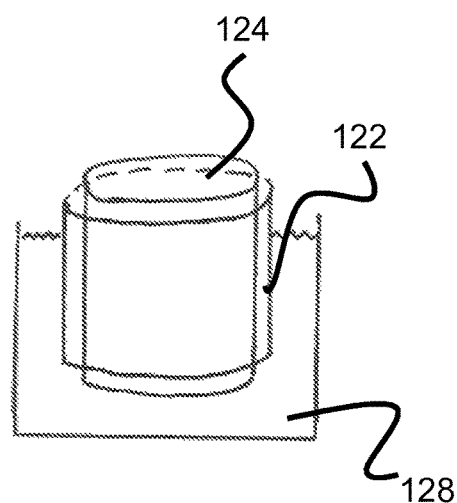
Figure 8C:
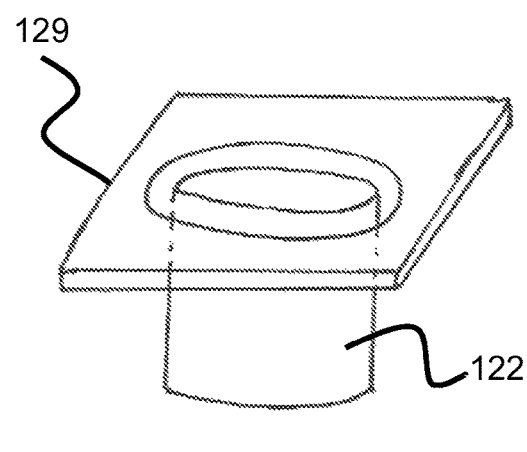
Figure 8D:
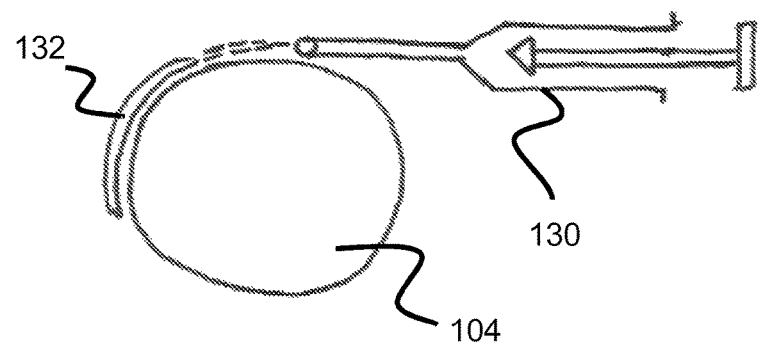
Figure 8E:
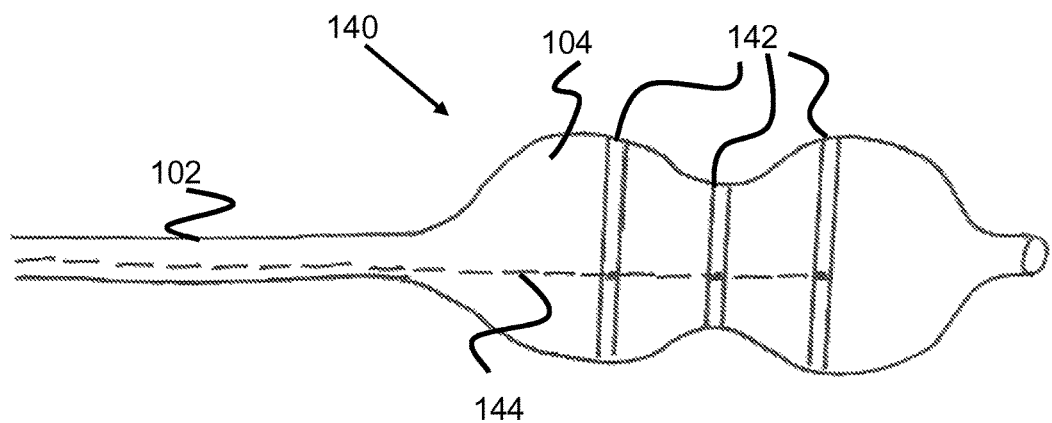

The echogenic film or band can also be formed from electrically conductive material such as copper, platinum, iron-containing metals, tungsten, nickel, tantalum, and others, as seen in the balloon embodiment 140 in FIG. 8E. Such conductive materials can be formed into a wire 142 that is bonded around an outside perimeter of the balloon. The wire 142 can be formed into a zig zag shape, a spiral shape, or other shape that will allow the wire to extend to a larger length to accommodate a diameter change of the balloon. Various polymer solutions or adhesives can be used to bond the wire to the balloon and provide insulation to the wire against current leakage. A small current that is controlled to approximately 5-300 milliamps (range 1 milliamp-1 amp) and provided to the wire via a current source located outside the body and connected to one or more wire bands (or other marker band embodiments) via a delivery wire 144 that runs through the shaft of the catheter and forms an electrical connection with each marker band or marker strip as shown in FIG. 8E. The current is supplied at a frequency that matches in some numerical multiple the frequency of the ultrasonic signal used to visualize the tissue, i.e., 2-20 MHz. The conducting material of the band can also be formed from electrically conductive particles that are embedded within a polymer matrix (including electrically conductive polymers including ionomers) that forms a band around the perimeter of the balloon. Upon application of the ultrasonic frequency current, the electrically conductive band 142 will send a signal that will be visualized via the ultrasound transducer. The conductive band will then be visualized as a ring that will provide information to the reviewer regarding the diameter and the orientation of the axis of the balloon which lies parallel to the axis of the band.

Figure 6B:
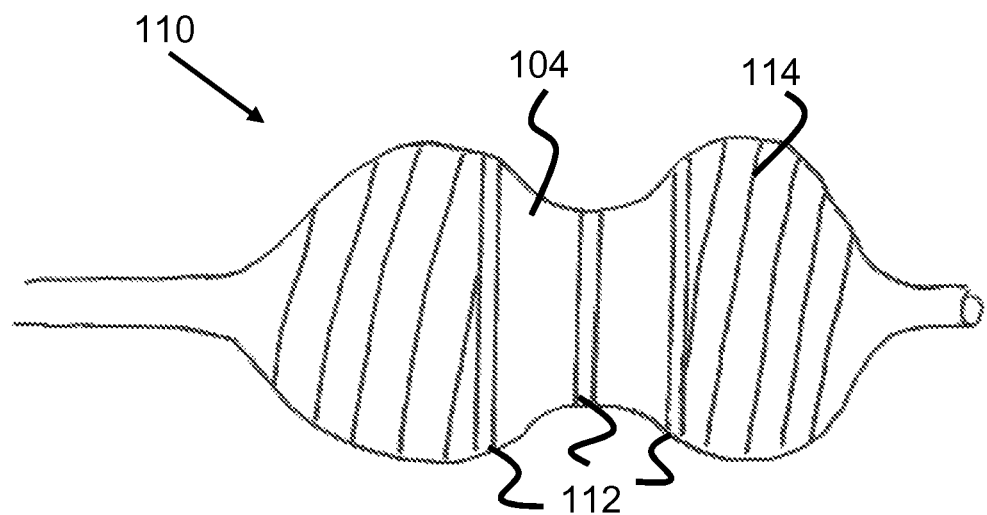
Figure 6C:
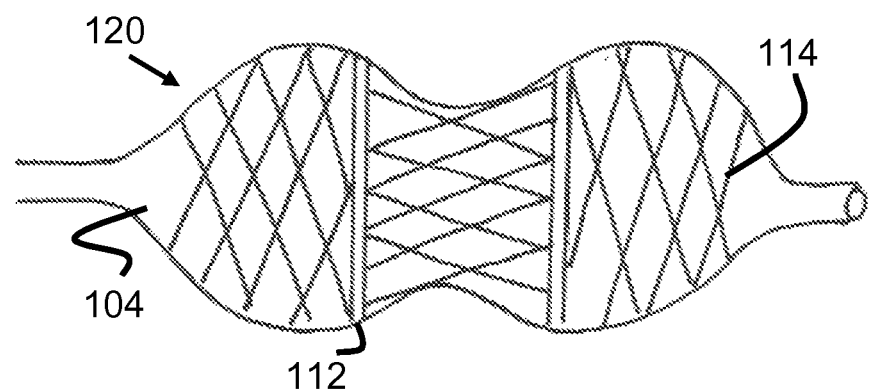

FIGS. 6B and 6C show embodiments 110 and 120 of the bulbous balloon 104 that are formed from a semi-compliant material such as Pebax, Nylon, Polyurethane, PET, silicone, or other material or composite material used in forming medical balloons. The bulbous regions of the balloon are wrapped, for example, in a spiral or braided fiber wrap 114 to ensure that the bulb diameter cannot grow appreciably during inflation. The angle of the fiber wrap is between 70-85 degrees (range 50-89 degrees) relative to the axis. As shown in FIG. 6C, the waist can also be wrapped, for example, in fiber although at a significantly lower angle with respect to the axis ranging from 20 to 45 degrees (range zero-60 degrees) relative to the axis. The lower angle of wrap in the waist by at least 10 degrees) allows the waist to grow in diameter but will restrict length growth as the balloon 104 is inflated to pressures of approximately 1-2 atm (range 0.5-3.5 atm). The waist diameter growth allows the waist to make contact with the annulus as the pressure is increased from 1.0 atm to approximately 2.5 atm. RO or echogenic marker bands can be placed in the waist and in the bulbous regions of the balloon in a manner similar to that described for FIG. 6A.

During use the balloon is located in the aortic sinus and LVOT with the balloon waist adjacent the annulus. Upon inflation of the balloon 104, the bulbs make contact with the tissues of the LVOT and the stenotic aortic valve leaflets located in the aortic sinus. The marker band located in the waist of the balloon determines the location of the annulus along the axis of the LVOT and aortic sinus. The fluoroscopy camera can be adjusted such that it is aligned directly parallel to the plane of the circle formed by the waist marker band and the marker band on the distal bulb located in the LVOT; the marker bands will appear as a line on the fluoro camera. The operator will therein know the location of the aortic annulus along the axis of the aortic root or aortic sinus and will also know the proper alignment of the axis of the aortic sinus, annulus, and LVOT (which is aligned with the bulbous balloon axis) so that placement of the TAVR device can be made with proper positioning and with proper alignment of the TAVR device axis with the axis of the LVOT.

In the embodiments having a waist that is significantly more compliant than the bulbs, including the embodiments shown, for example, in FIGS. 6A-6C, the device can also be used to more accurately determine the diameter of the annulus. The balloon can be inflated to a pressure that causes the waist to come into contact with the annulus; this is typically between 0.6-1 atm (range 0.5-3.5 atm). The image of the annulus can be taken via fluoroscopy or via 2D echo or via 3D echo to view and measure the diameter of the marker bands located around the circumference of the balloon waist.

On 3D echo a transverse view will show a echogenic ring that is known to be in contact with the annulus (based on known compliance curves for the balloon waist); this ring can be traced using planimetry to determine the area of the annulus in a stretched condition and determine the effective diameter of a circle with the same area. From this diameter measurement, the properly sized TAVR device can be chosen such that the TAVR device size will not lead to perivalvular leakage or lead to TAVR migration. The techniques described in the Ellipticity Measuring Device application, Ser. No. 13/766,464 for RO markers have application as well to the echogenic markers of the present application. 3D echo will provide improved capability over fluoroscopy in determining the ovality of an annulus via examination of a transverse view of the annulus. The echogenic markers will help to ensure that the view that is being evaluated is indeed along the plane of the marker band and hence is perpendicular to the axis of the aortic sinus, aortic annulus, and LVOT. The use of echo markers can also obviate the need for large unwanted contrast medium delivery to the patient and allow visualization of the balloon with a reduced amount of contrast or no contrast medium delivery.

From fluoroscopy or from echogenic images, the diameter of the annulus can be identified in one longitudinal view provided that the annulus has been exposed to adequate forces to provide a round cross-sectional shape to the annulus. Alternately, a second orthogonal fluoroscopic view can be taken to provide a second measurement of the annulus from which an average annulus diameter can be determined.

The RO or echogenic marker bands also provide benefits to the operator who is using the balloon for post dilation of a TAVR device. The ability to view the RO or echogenic ring that is in contact with a calcium nodule can assist the operator in evaluating the extent and location of the calcium nodule protrusion and whether further dilation may be warranted to reduce, for example, perivalvular leak around the TAVR device. A calcium nodule located in a tight LVOT may suggest that further post dilation of the TAVR device would not be advisable due to possible rupture of the native tissue. A small nodule located, for example, in a large diameter aortic sinus may suggest that further post dilation would be warranted to reduce perivalvular leakage. The balloon described in FIGS. 6A-6C can also be used to measure the diameter of an annulus of a valve of the heart. A bulbous balloon can be formed, for example, from an elastomeric material such as polyurethane that has a great deal of elongation. The balloon can have a bulb diameter that is 3-6 mm larger (range 2-10 mm larger) than the waist at pressures that are approximately 0.5 atm (range 0.3-1 atm). The bulbous shape of the balloon allows the balloon waist to automatically position itself across and adjacent to the annulus. At pressures above approximately 0.5 atm (range 0.5-1.5 atm) the waist can grow in diameter and make contact with the annulus. The presence of marker bands around the perimeter of the waist allows the diameter of the annulus to be measured by observation of marker band under fluoro or echo. Marker bands around the perimeter of one or more of the bulbs allows the physician to determine the ovality of the annulus.

Figure 7A:
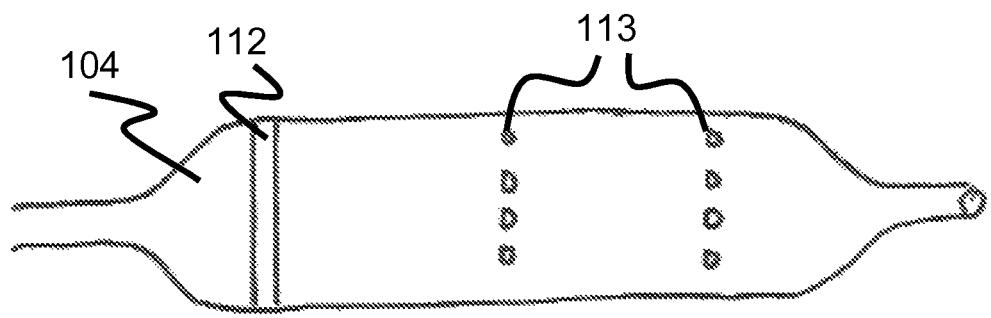
Figure 7B:
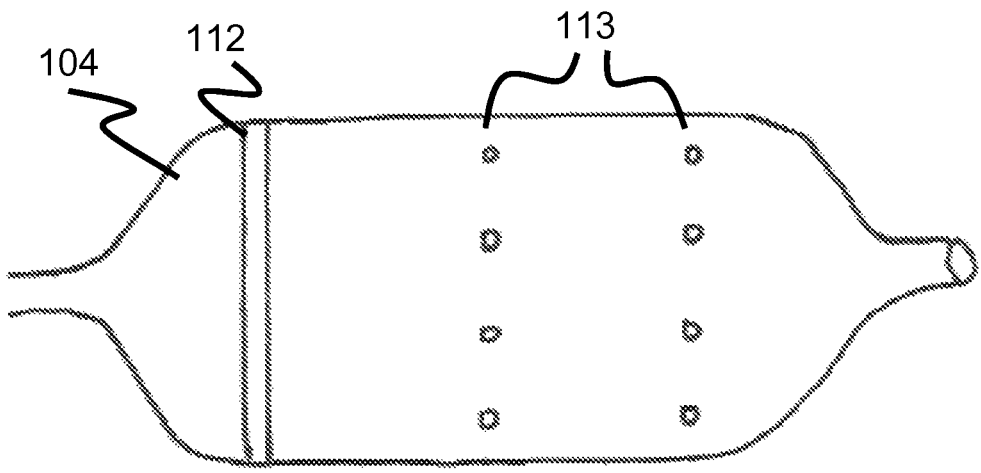

FIGS. 7A and 7B show a cylindrical balloon having either an RO marker band 113, echogenic marker band 112, or both located around its circumference. The marker bands can be place at several locations along the length of the balloon 104. The marker bands can be solid marker bands or discontinuous marker bands. As the balloon is inflated, as shown in FIG. 7B, the marker bands 112, 113 stretch and come into contact with the annulus and the stenotic leaflets of the heart. The diameter of the balloon and alignment of the balloon within the aortic sinus and LVOT can be observed on fluoro or via 2D or 3D echo. The position of the balloon 104 relative to the axial position of the annulus is not determined automatically with this balloon as it is with the bulbous balloon. Expansion of the cylindrical balloon formed from a semi-compliant or compliant material such as a polyurethane or softer lower durometer Nylon or Pebax would allow an indent to be observed in the balloon at the location of the annulus. The location of the indent could be used to identify the position of the annulus. The marker bands can be used as described for the bulbous balloon to determine the axial alignment and to improve the diameter measurement via fluoroscopy or via echo.

As the balloon is expanded from its smaller diameter configuration shown in FIG. 7A to the expanded configuration shown in FIG. 7B, the distance between individual neighboring dots or dashes of the discontinuous band will separate further from each other proportional to the diameter increase of the balloon and can thereby be used to determine the diameter of the annulus or tissue that is adjacent the marker band or in contact with it.

FIG. 8A shows one method for forming a circular marker band that could be applied to the balloon 104 via solvent bonding or adhesive as a second step. In this method a cylindrical mandrel 124 is first surrounded by a thin polymeric sheath 122 having a thickness of less than 0.001 inch. The thin sheath can be formed via a thin film blowing process followed by a sizing (involving thermal stretching, for example) step to make it fit snugly over the cylindrical mandrel 124. The material of the sheath can be the same or compatible with the solvent bonding capability to the polymeric suspension containing RO or echogenic material that is to be deposited onto its circumferential surface of the balloon. Alternately, the sheath should be compatible with the solvent bonding characteristics of the balloon over which it will eventually be located and bonded onto the balloon surface. Alternately, the cylindrical mandrel can be formed of a material, such as Teflon, for example, that does not easily adhere to the band material; in this case a sheet would not be necessary. The cylindrical mandrel is rotated while a RO or echogenic suspension is applied to the outside of the thin sheath 122. A doctor knife 126 is located adjacent one edge of the cylinder 124 to force the suspension into a thin film over the sheath 122. After the solvent from the suspension has evaporated (or chemical reaction has occurred), a thin deposit remains on the sheath 122 or the cylindrical mandrel, the deposit is a mixture of RO or echogenic material embedded within a polymeric material. The polymeric material can be one that is similar to the material of the balloon to enhance solvent boding to the balloon is a secondary step.

The sheath or the thin deposited and cured material can then be slid off of the mandrel 124 and cut into strips of either RO band or echogenic band. The strips can have a width of approximately 1 mm (range 0.5-3 mm). The strips can be placed over the balloon in an appropriate location and bonded to the outer surface of the balloon via solvent bonding or via adhesive.

Figure 9A:
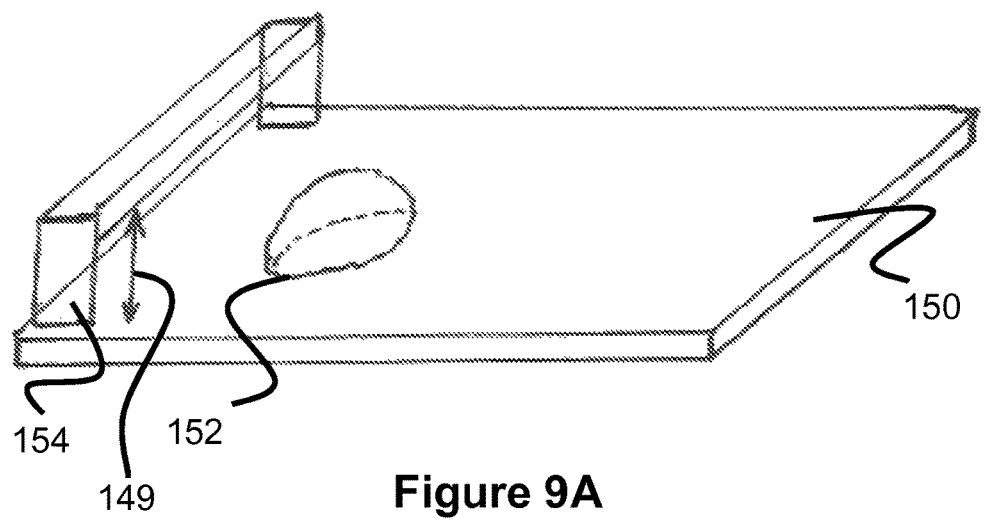
Figure 9B:
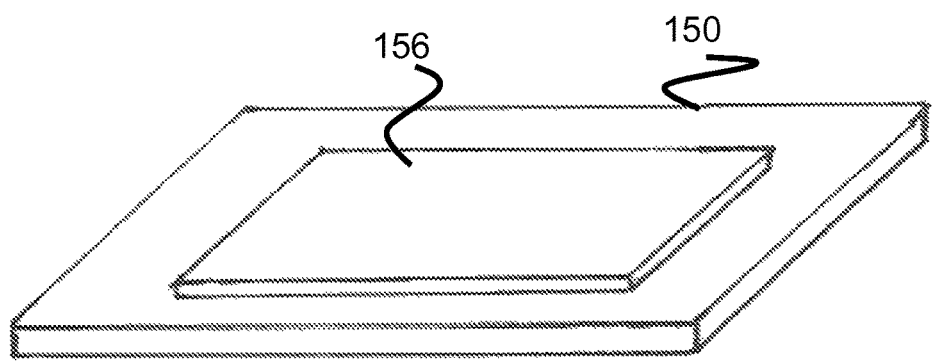
Figure 9C:
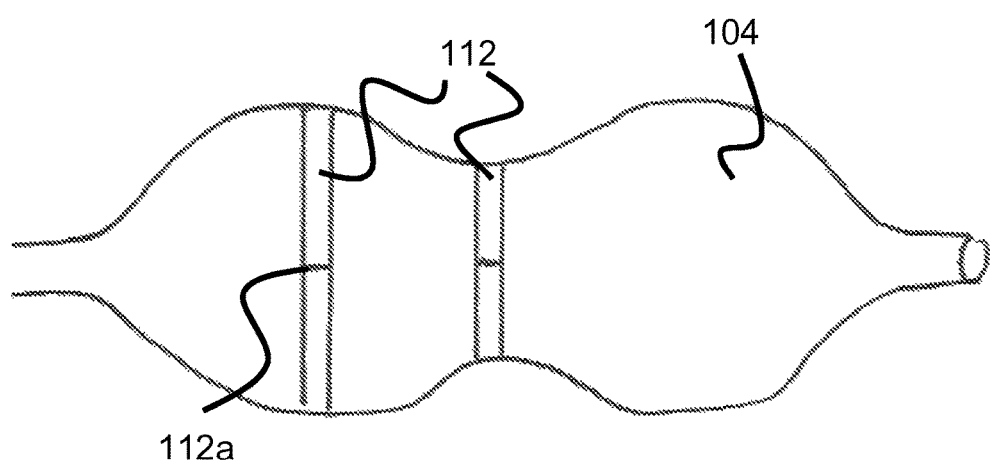

A thin flat film of RO or echogenic material suspension can also be formed by placing a specified amount of suspension 152 of polymer, solvent, and particles onto a flat planar plate 150 as shown in FIGS. 9A-9C. A flat doctor blade 152 located at a set distance or gap 149 from the plate 150 is pulled across the suspension material 152 to form a uniform layer of the suspension. After allowing the solvent to evaporate, the remaining polymer and particle film 156 can be cut into strips 112 that are bonded around the perimeter of the balloon 104 as described earlier. The end of the strip or marker band can form a junction or seal 112a that can be bonded in a continuous manner such that it is not visualized, if desired.

An alternate embodiment for forming circular rings of RO or echogenic bands is shown in FIGS. 8B and 8C. In this method a cylindrical mandrel 124 having a sheath 122 applied to its outer surface (or alternately without a sheath applied) is dipped into a container 128 having a suspension of RO or echogenic material within a polymeric solution. Following removal from the container as shown in FIG. 8C, a circular doctor blade 129 or bed knife is pulled downward to generate a thin film of marker band around the sheath. The marker band material is then cured via solvent evaporation and molecular bonding and cut into strips that are applied to the outside of the balloon as described earlier.

Alternate methods for forming marker bands are contemplated. Echogenic marker band methods include creating a foamed polymer via salt leaching or gas penetration to thereby leave voids of air that are very echogenic. Alternately one can process a polymeric solution having a non-aqueous solvent with addition of a water soluble or immiscible liquid or polymer material to form a suspension or emulsion; placing the suspension into an aqueous bath will allow the diffusion of aqueous portion from the suspension leaving a porous polymeric film that will be echogenic.

Other echogenic coatings have been contemplated including placing small metal, polymeric spheres, flat metal or flat polymeric flakes into a solution of polymer and solvent to form a suspension that can be formed into a thin film and used as either RO marker bands or echogenic marker bands. Also placing a metallic wire formed into a zig zag shape or spiral shape around the balloon would provide echogenic character while not restricting expansion of the balloon as described earlier.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A bulbous balloon for post dilating a stent structure that has been implanted in a human body, said balloon comprising:
   A. a fully inflated distal bulb section that is at least 3 mm larger in diameter than a fully inflated diameter of a proximal balloon section;
   B. a waist portion located between the distal bulb section and the proximal balloon section, and the waist portion retaining a smaller fully inflated diameter than a fully inflated diameter of said proximal balloon section;
   C. said balloon having a stent located over said waist portion and over said distal bulb section that is adjacent to the proximal balloon section, said stent being expandable from a small diameter configuration to a larger diameter configuration and is configured for generating an outward force against the stent structure during expanding to cause the stent structure to move outwards;

D. said balloon being configured such that said proximal balloon section applies a smaller force outwards against surrounding tissues than a force applied by said distal bulb section against surrounding tissues.

2. A bulbous balloon of claim 1, wherein as the bulbous balloon is fully inflated, said stent makes contact along its perimeter with the stent structure to force the stent structure outwards thereby reducing or eliminating a gap between the stent structure and tissues surrounding the stent structure and thereby reducing leakage of blood around the stent structure.

3. The bulbous balloon of claim 2, wherein said distal bulb section is formed from a braided structure, said braided structure providing for enlargement in diameter as the length is reduced, the braided structure providing for blood flow through said distal bulb section, said distal bulb section being slidable with respect to said proximal balloon section.

4. The bulbous balloon of claim 2, wherein said distal bulb section is a distal balloon section that shares a same luminal space as the proximal balloon section.

5. The bulbous balloon of claim 2, wherein said distal bulb section is a distal balloon section having a separate luminal space from said proximal balloon section, said distal balloon section being configured to be inflated via a separate inflation lumen prior to said proximal balloon section.

6. The bulbous balloon of claim 1, wherein the stent is located on said distal bulb section, and a length of the portion of the distal bulb section that the stent covers is not greater than a length of an another portion of the distal bulb that is not covered by the stent, and wherein the lengths of the portion and the another portion are measured along a longitudinal direction of the balloon.

7. A bulbous balloon for performing valvuloplasty on a valve of the heart, said balloon comprising:
A. a fully inflated distal balloon portion that is at least 3 mm larger in diameter than a fully inflated diameter of a proximal balloon portion; a waist portion located between the distal balloon portion and the proximal balloon portion, and the waist portion retaining a smaller fully inflated diameter than a fully inflated diameter of said proximal balloon portion;
B. said balloon having a marker band in the form of stretchable wire located along a perimeter of said proximal balloon portion;
C. said balloon configured to position said distal balloon portion upstream of the annulus;
D. said balloon configured to place said proximal balloon section adjacent the valve annulus;
E. said balloon being configured such that said proximal balloon portion applies a smaller force outwards against the annulus than a force applied by said distal balloon portion against the surrounding tissues of the heart valve; and,
F. a stent disposed over said waist portion and one of said proximal balloon portion or said distal balloon portion.

8. The bulbous balloon of claim 7, wherein said marker band is a radiopaque band formed from metal particles embedded in a polymer matrix and bonded to the outside surface of the balloon.

9. The bulbous balloon of claim 7, wherein said marker band is an echogenic band formed from an echogenic material bonded to an outside surface of the balloon.

10. The bulbous balloon of claim 9, wherein said echogenic material comprises echogenic particles formed from flat metal particles embedded in a polymer matrix.

11. The bulbous balloon of claim 9, wherein said echogenic material comprises echogenic particles formed from gas-filled particles.

12. The bulbous balloon of claim 9, wherein said echogenic material comprises echogenic particles having a natural frequency of 2 to 20 MHz and absorb and reflect sound waves.

13. The bulbous material of claim 9, wherein said echogenic material comprises a conductive material, said conductive material being provided with a current that has a frequency ranging from 2 to 20 MHz.

14. The bulbous balloon of claim 13, wherein said conductive material comprises metal particles embedded in a polymer matrix formed from a conductive polymer.

15. The bulbous balloon of claim 13, wherein said conductive material comprises a conductive metal wire bonded to the outside surface of the balloon, said wire being formed into a configuration that allows for diametric expansion of said balloon.

16. The bulbous balloon of claim 7, wherein the marker band is a conductive wire.

17. The bulbous balloon of claim 7, wherein the marker band is a wire in a zig-zag shape or a spiral shape.

18. A bulbous balloon for performing valvuloplasty, the bulbous balloon comprising:
A. a proximal balloon portion;
B. a distal balloon portion has a fully inflated diameter that is at least 3 mm larger than a fully inflated diameter of the proximal balloon portion;
C. a waist portion located between the distal balloon portion and the proximal balloon portion, and the waist portion retaining a smaller fully inflated diameter than a fully inflated diameter of said proximal balloon portion;
D. a marker band located along a perimeter of the balloon, the marker band being a discontinuous band comprised of a series of dots or dashes that extend around a circumference of the balloon;
E. a stent disposed over said waist portion and over said distal balloon portion and/or said proximal balloon portion.

19. The bulbous balloon of claim 18, wherein the marker band is a radiopaque band formed from metal particles embedded in a polymer matrix and bonded to the outside surface of the balloon.

20. The bulbous balloon of claim 18, wherein the marker band is an echogenic band formed from an echogenic material bonded to an outside surface of the balloon.

21. The bulbous balloon of claim 18, wherein the bulbous balloon comprises a second marker band, and the two marker bands are respectively located on perimeters on the proximal balloon portion and the distal balloon portion.

22. The bulbous balloon of claim 21, wherein the second marker band is a solid or continuous band.

23. The bulbous balloon of claim 21, wherein the second marker band is a discontinuous band comprised of a series of dots or dashes that extend around a circumference of the balloon.

24. The bulbous balloon of claim 18, wherein the bulbous balloon comprises a second marker band and a third marker band, the three marker bands are respectively located on the proximal balloon portion, the distal balloon portion and the waist portion.

25. The bulbous balloon of claim 24, wherein at least one of the second marker band and the third marker band is a solid or continuous band.

26. The bulbous balloon of claim 25, wherein at least one of the second marker band and the third marker band is a discontinuous band comprised of a series of dots or dashes that extend around a circumference of the balloon.

* * * * *